United States Patent [19]
Bogdanović et al.

[11] Patent Number: 6,117,372
[45] Date of Patent: Sep. 12, 2000

[54] METHOD OF SYNTHESIZING GRIGNARD COMPOUNDS USING CATALYSTS

[75] Inventors: Borislav Bogdanović; Manfred Schwickardi, both of Mülheim an der Ruhr, Germany

[73] Assignee: Studiengesellschaft Kohle mbH, Mulheim An der Ruhr, Germany

[21] Appl. No.: 09/214,369

[22] PCT Filed: Jul. 3, 1997

[86] PCT No.: PCT/EP97/03516

§ 371 Date: Jan. 5, 1999

§ 102(e) Date: Jan. 5, 1999

[87] PCT Pub. No.: WO98/02443

PCT Pub. Date: Jan. 22, 1998

[30] Foreign Application Priority Data

Jul. 12, 1996 [DE] Germany .................. 196 28 159

[51] Int. Cl.$^7$ ................. C07F 3/00; C07F 3/02
[52] U.S. Cl. .......................................... 260/665 G
[58] Field of Search ........................ 260/665 G

[56] References Cited

FOREIGN PATENT DOCUMENTS 0 469 463  2/1992  European Pat. Off. .

OTHER PUBLICATIONS

Chemistry of Materials by Aleandri et al vol. 7, No. 6, pp. 1153–1170, Jun. 1995.

B. Bogdanovic: "Magnesium Anthracene Systems and their Application in . . . ", Accounts of Chemical Research., vol. 21, No. 7, —1988 Washington US, pp. 261–267, XP002041372.

Bogdanovic B et al: "Use of magnesium anthracene.cntdot. 3 THF in synthesis: generation of Grignard . . . " Chem. Ber. (CHBEAM,00092940);90; vol. 123 (7); pp. 1507–15, Max–Planck–Inst.Kohlenforsch.;Muelheim an Der Ruhr; D–4300; Fed.Rep.Ger.(DE), XP002041373 (1990).

Bogdanovic B et al: "Magnesium anthracene systems. 8. Magnesium adducts of substituted anthracenes–preparation and properties" Chem. Ber. (CHBEAM,00092940);90; vol. 123(7); pp. 1529–35, Max–Planck–Inst.Kohlenforsch.;Muelheim an Der Ruhr; D–4330/1; Fed.Rep.Ger.(DE), XP002041374 (1990).

Bartmann E et al: "Magnesium anthracene systems. 7. Active magnesium from catalytically prepared . . . " Chem. Ber. (CHBEAM,00092940);90; vol. 123(7);pp. 1517–28, Max–Planck–Inst.Kohlenforsch.;Muelheim an Der Ruhr; D–4330;Fed.Rep.Ger.(DE), XP002041375 (1990).

S. Itsuno: "The First Direct Formation of a Grignard Reagent on an Insoluble Ploymer" Journal of Organic Chemistry., vol. 52, No. 20, —1987 Easton US, pp. 4644–4645, XP002041376.

*Primary Examiner*—Jean F Vollano
*Attorney, Agent, or Firm*—Norris, McLaughlin & Marcus, P.A.

[57] ABSTRACT

Grignard compounds from aromatic chlorine compounds and magnesium metal in the presence of a transition metal/magnesium chloride complex as a catalyst.

11 Claims, No Drawings

METHOD OF SYNTHESIZING GRIGNARD COMPOUNDS USING CATALYSTS

This application is the national phase of PCT/EP97/03516, filed Jul. 3, 1997, now WO 98/02443.

The present invention relates to a process for the preparation of Grignard compounds from organic halides and metallic magnesium in the presence of catalysts.

Grignard compounds are usually prepared by reacting organic halides with magnesium in an ether solvent; in certain cases, they may also be prepared in hydrocarbons (Comprehensive Organometallic Chemistry II, Vol. 1, 1995, p. 58–63; Comprehensive Organometallic Chemistry I, Vol. 1, 1982, p. 155; Chem. Ber. 1990, 123, 1507 and 1517).

However, a wide variety of organic halogen compounds exist, including, in particular, aromatic and vinylic chlorine compounds, with which the Grignard reaction proceeds only hesitantly, has low yields, or hardly succeeds at all. To increase the reactivity of magnesium towards such halides, a number of methods is known which are based on physical (grinding, ultrasonic treatment, metal evaporation) or chemical (entrainment method, Rieke method, dehydrogenation of magnesium hydride, reversible formation of magnesium anthracene) activation of the magnesium (Active Metals—Preparation, Characterization, Applications, Ed. A. Fürstner, VCH, 1996). Anthracene or magnesium anthracene and their derivatives are known as catalysts for the Gringnard reaction; however, they can be used only in the case of allyl, propargyl and benzyl halides (Chem. Ber. 1990, 123, 1507). The drawbacks of the mentioned methods are that they are either relatively cumbersome and expensive, or limited in their applicability or effects, or result in a higher consumption of magnesium (the entrainment method: J. Org. Chem. 1959, 24, 504). Therefore, there is still a need for effective and economical methods for the preparation of Grignard compounds from the above mentioned inert organic halogen compounds which are not subject to the mentioned drawbacks, and with the proviso that conventional, commercial magnesium types can be used.

Surprisingly, it has now been found that highly effective catalysts for the conversion of aromatic chlorine compounds, chlorine-containing polymers and other less reactive organic chlorine compounds to the corresponding Grignard compounds using commercial Mg powders or turnings can be produced using the so-called inorganic Grignard reagents of the transition metals (U.S. Pat. No. 5,385,716, Studiengesellschaft Kohle, 1995), optionally in combination with cocatalysts according to the invention. Those systems based on metals of groups 4 to 10 of the Periodic Table, especially Fe, Mn, Cr and Mo, are considered catalytically active, inter alia; of these, Fe and Mn catalysts are especially effective. The catalysts are preferably produced in situ by reacting the respective metal halides with excess Mg metal in tetrahydrofuran (THF), monoglyme or diglyme, in accordance with the preparation method for inorganic Grignard reagents (see above). As cocatalysts, there may be used, in particular, 9,10-diphenylanthracene (DA) and/or its magnesium adducts (Chem. Ber. 1990, 123, 1529) and magnesium halides. The system consisting of DA, $FeCl_2$ or $MnCl_2$, $MgCl_2$ and excess Mg powder in THF, monoglyme or diglyme has proven to be particularly active as a catalyst. The reactions with organic chlorine compounds are preferably performed from room temperature to the boiling temperature of the solvent.

In one embodiment, the present invention relates to a process for preparing Grignard compounds comprising reacting an organic halide with magnesium metal in an ether solvent in the presence of an inorganic Grignard reagent catalyst of the formula $[M(MgCl)_m(MgCl_2)_n]$, wherein M represents a transition metal of groups 4 to 10 of the Periodic Table, m represents 1, 2 or 3, and n represents 0 or 1, and optionally in the presence of a cocatalyst comprising anthracene or substituted anthracenes or their magnesium adducts and/or magnesium halides. The organic halide may be, for example, an aromatic compound or a chlorine-containing polymer. The ether solvent may be, for example, tetrahydrofuran, monoglyme or diglyme. The reaction may be performed, for example, at temperatures ranging from 0° C. to the boiling point of the solvent employed. The magnesium metal may be, for example, in the form of a finely divided magnesium powder, which may, for example, have a mesh size which is, preferably, greater than 200 up and to a maximum of 270. Also, a cocatalyst, for example, diphenylanthracene, may be used. In a particular embodiment, the present invention relates to a process for preparing Grignard compounds comprising reacting an organic chlorine compound with magnesium powder in the presence of an inorganic Grignard reagent catalyst prepared by reacting $FeCl_2$ or $MnCl_2$ and 9,10-diphenylanthracene, $MgCl_2$ and excess magnesium powder in tetrahydrofuran, monoglyme or diglyme. The inorganic Grignard reagent catalyst may also be prepared, for example, by a process comprising reacting $CrCl_3$ or $MoCl_5$ with magnesium metal.

The invention will be further illustrated by way of the following Examples without being limited thereto.

The experiments described in the following were performed in an argon atmosphere. The solvents used were deaerated and anhydrous. THF is conveniently dried over magnesium anthracene.3 THF. Commercial Mg powder (270 mesh) was used in all experiments. For this purpose, anhydrous $MgCl_2$ was prepared from 1,2-dichloroethane and magnesium powder in THF.

EXAMPLE 1

Under vacuum (0.1 mbar), 3.70 g (150 mmol) of Mg powder was baked out (100–150° C.) and, after cooling, 50 ml of THF and 2 to 3 drops of ethyl bromide was added, and the mixture was stirred at room temperature (RT) for 1 h. Subsequently, 0.26 g (2 mmol) of anhydrous $FeCl_2$, 20 ml of THF and 10.2 ml of an 0.49 M solution of $MgCl_2$ in THF (5 mmol) was added. After 30 min of stirring, the solution turned brown (formation of the inorganic Grignard reagent, $[FeMgCl.0.5\ MgCl_2]$). Thereupon, 13.6 ml (100 mmol) of 1-chloronaphthalene (dried over molecular sieve) was added dropwise to the suspension within 30 min with stirring which caused the reaction mixture to warm up to 62 °C. After another 2 hours of stirring the mixture, the yield of 1-naphthylmagnesium chloride as determined by acidimetric titration of a 2.0 ml sample of the filtered solution (total volume 95 ml) was 62%, after 19 h, it was 66%, and after 45 h, it was 67%. A 10 ml sample of the solution was protolysed with ethanol, and the volatiles were distilled off under high vacuum (bath temperature of up to 200° C.). After adding a known amount of n-hexadecane as a standard, the distillate was analyzed by gas chromatography. In addition to binaphthyl, 0.88 g of naphthalene (65%, based on 1-chloronaphthalene) was found; 1-chloronaphthalene could not be detected.

In a corresponding comparative experiment without addition of $FeCl_2$, no reaction of 1-chloronaphthalene with Mg powder had occurred after 2 h.

EXAMPLES 2–4

The experiments were performed by analogy with Example 1 using $MnCl_2$, $CrCl_3$ and $MoCl_5$, respectively ($MCl_n$, Table 1) as catalyst components instead of $FeCl_2$.

TABLE 1

| $MCl_n$ | reaction temperature [° C.] | yield of 1-$C_{10}H_7MgCl$[a], % (reaction time in h) | |
|---|---|---|---|
| $MnCl_2$ | 23–62 | 62 (2) | 66.5 (19) |
| $CrCl_3$ | 23–33 | 16 (2) | 28.5 (21) |
| $MoCl_5$ | 25 | 6 (2) | 20 (22) |

[a] as determined by acidimetric titration.

EXAMPLE 5

Under vacuum (0.1 mbar), 3.70 g (150 mmol) of Mg powder was baked out (100–150° C.) and, after cooling, 0.66 g (2 mmol) of 9,10-diphenylanthracene (DA, Aldrich), 50 ml of THF and 2 to 3 drops of ethyl bromide was added. After stirring the mixture for 1 h, a deep-blue solution had formed (formation of the Mg-DA radical anion, see description). To this solution, 0.26 g (2 mmol) of anhydrous $FeCl_2$, 20 ml of THF and 10.2 ml of an 0.49 M solution of $MgCl_2$ in THF (5 mmol) was added, followed by stirring for another 30 min. Thereupon, 13.6 ml (100 mmol) of 1-chloronaphthalene was added dropwise within 30 min, the color of the solution turning from deep-blue to brown, and the solution warming up to 55° C. After 2 h of stirring, the yield of the Grignard compound of 1-chloronaphthalene was 63%, and after 5 h, it was 67% (as determined by acidimetric titration). The protolysis of a 10 ml sample of the solution (total volume 95 ml; cf. Example 1) yielded 0.92 g of naphthalene (corresponding to a yield of 1-$C_1OH_7MgCl$ of 68%), binaphthyl and no other products (GC analysis).

EXAMPLE 6

The experiment was performed by analogy with Example 5 using monoglyme as the solvent instead of THF. The maximum reaction temperature was 64° C. One hour after the completion of the dropwise addition of 1-chloronaphthalene, a voluminous precipitate formed. The solvent was evaporated in vacuo, the residue was dissolved in 100 ml of THF, and the suspension was filtered. The yield of 1-naphthylmagnesium chloride as determined by acidimetric titration was 80%.

EXAMPLE 7

The experiment was performed by analogy with Example 5 using diglyme as the solvent instead of THF. The maximum reaction temperature was 70 ° C. The processing of the products was performed as described for Example 6. After 1 h of reaction, the yield of 1-naphthylmagnesium chloride was determined by acidimetric titration to be 81%.

EXAMPLES 8–12

The experiments (see Table 2) were performed by analogy with Example 5.

Table 2: Catalytic preparation of Grignard compounds from aliphatic and aromatic chlorine compounds and chlorine containing polymers and magnesium in THF

| Ex. No. | organic chlorine compound [mmol] | total volume of solution [ml] | reaction time[a] [h] | reaction temp. [° C.] | yield of Grignard compound or Cl conversion [%] | reference |
|---|---|---|---|---|---|---|
| 8 | $(H_3C)_3CCH_2Cl$[100] | 92 | 2 | 24–61 | 100[b] | 1) |
| 9 | ![structure with O(CH2)6Cl] [100] | 100 | 1 | 20–60 | 83[b,c] | 2) |
| 10 | —[$CH_2CHCl$]$_x$—[d] [100] | 165 | 4 | 20–25 | 25[e,f] | |
| 11 | $C_6H_5Cl$ [100] | 90 | 2 | 20–60 | 100[b] | 3) |
| 12 | —[$CH_2CH(p-C_6H_4CH_2Cl)$]$_x$—[g] [15.3] | 85 | 2 6 | 20–25 b.p. | 60[e] 95[e] | 4) |

[a] After completion of halide addition.
[b] Grignard determination by acidimetric titration.
[c] After another 22 h at RT, the yield of the Grignard compound remained unchanged.
[d] 6.25 g of polyvinyl chloride powder (Aldrich).
[e] In this case, the determination of the conversion was effected by titration of Cl⁻ ions by the Volhard method.
[f] The reaction was performed in a glass ball mill. In the course of the reaction, the reaction mixture became increasingly viscous.
[g] 11.45 g of p-chloromethylpolystyrene ("Bio-Beads" SX1, 200–400 mesh, 1.34 mmol of Cl/g); in this case, the experiment was performed with 46 mmol of Mg powder, 0.8 mmol of DA, 0.8 mmol of FeCl$_2$ and 2 mmol of MgCl$_2$.

1) J. Org. Chem. 1967, 32, 1233.
2) Bull. Chem. Soc. Jpn. 1976, 49, 1989.
3) J. Am. Chem. Soc. 1972, 94, 7178.
4) J. Org. Chem. 1987, 52, 4644.

EXAMPLE 13

Catalytic Preparation of 1-naphthylmagnesium Chloride With FeI$_2$

The experiment was performed by analogy with Example 1 using anhydrous FeI$_2$ as a catalyst component instead of FeCl$_2$. The maximum reaction temperature was 44° C. After 2 h of reaction, the yield of 1-naphthylmagnesium chloride was determined by acidimetric titration to be 53%.

EXAMPLE 14

Catalytic Preparation of 1-naphthylmagnesium Chloride With PtCl$_2$

The experiment was performed by analogy with Example 1 using anhydrous PtCl$_2$ as a catalyst component instead of FeCl$_2$. The maximum reaction temperature in the course of this experiment was around 36° C. After 10 h of reaction, the yield of 1-naphthylmagnesium chloride as determined by acidimetric titration was 40%.

EXAMPLE 15

Catalytic Preparation of 1-naphthylmagnesium Chloride With Ru(MgCl)$_3$

In this experiment, the separately prepared inorganic Grignard reagent Ru(MgCl)$_3$ was used as a catalyst instead of a transition metal halide. The Ru(MgCl)$_3$ solution was prepared from active magnesium metal and RuCl$_3$ according to the U.S. Pat. No. 5,385,716 of the Studiengesellschaft Kohle (1995).

To 3.70 g (150 mmol) of magnesium powder was added 20 ml of THF and 3 drops of ethyl bromide, and the mixture was stirred at room temperature for 1.5 h. Subsequently, 11 ml (2.0 mmol) of an 0.182 M Ru(MgCl)$_3$ solution in THF was added. The dark brown solution was stirred for another 20 min, diluted with 50 ml of THF, and then 13.6 ml (100 mmol) of 1-chloronaphthalene was added dropwise within 1 h with stirring. This caused the inside temperature to rise from 20 to 29° C. After another 6 hours of stirring the mixture, the yield of 1-naphthylmagnesium chloride as determined by acidimetric titration of the filtered solution was 27%.

In a corresponding comparative experiment in which RuCl$_3$ was added instead of the Ru(MgCl)$_3$ solution, the yield was <5%.

EXAMPLE 16

Preparation of the Grignard Compound of 1,3-dibenzyl-2-(4-chlorophenyl)imidazolidine With FeCl$_2$ and Isolation as a TMS Product To 2.0 g (82 mmol) of magnesium powder was added 12 ml of THF and 4 drops of ethyl bromide, and the mixture was stirred at room temperature for 1.5 h. Subsequently, 150 mg (1.18 mmol) of FeCl$_2$ was added, followed by stirring for another 60 min. The mixture turned deep brown. Then, without another addition of a cocatalyst, a solution of 18.9 g (52.1 mmol) of 1,3-dibenzyl-2-(4-chlorophenyl) imidazolidine in 33 ml of THF was added dropwise within 1 h at a bath temperature of 45° C. At this temperature, the mixture was intensely stirred with a metal blade stirrer for another 4 h. After cooling, the mixture was filtered through a D4 frit, and 8.0 ml (63 mmol) of chlorotrimethylsilane was added dropwise to the filtrate at room temperature within 30 min, whereupon an exothermic reaction took place. The mixture was further stirred at 20° C. for several hours, concentrated in an oil-pump vacuum, and the residue was dried at 20° C./0.1 mbar for 20 min. The residue was then extracted with pentane under argon, the precipitate was filtered off through a D4 frit, and the light yellow filtrate was concentrated in an oil-pump vacuum. After 2 hours of drying at 20° C./0.1 mbar, 20.0 g of a slightly yellowish powder was obtained which was identified as 1,3-dibenzyl-2-(4-trimethylsilylphenyl)imidazolidine by MS, IR and NMR spectra (see equation). The purity of the product obtained was 91.1% as determined by gas chromatography which corresponds to an isolated yield of 87%.

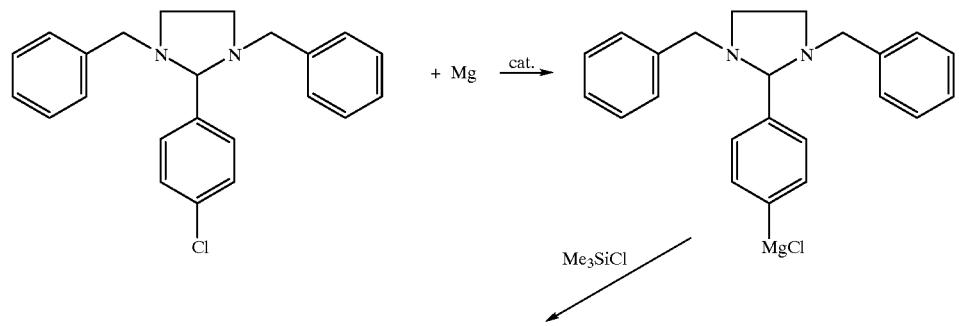

-continued

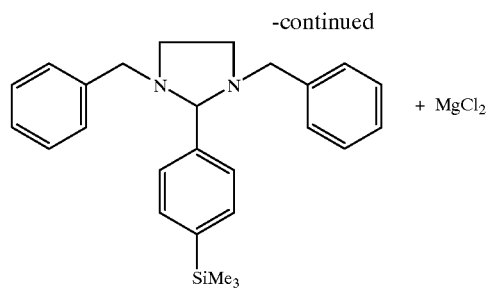 + MgCl$_2$

What is claimed is:

1. A process for the preparation of Grignard compounds comprising reacting an organic halide with magnesium metal in an ether solvent in the presence of an inorganic Grignard reagent catalyst prepared by a process comprising reacting a transition metal halide with magnesium metal, wherein said transition metal is a transition metal of groups 4 to 10 of the Periodic Table.

2. A process according to claim 1, which comprises reacting an organic halide with magnesium metal in an ether solvent in the presence of an inorganic Grignard reagent catalyst of the formula [M(MgCl)$_m$(MgCl$_2$)$_n$], wherein M represents a transition metal of groups 4 to 10 of the Periodic Table, m represents 1, 2 or 3, and n represents 0 or 1, and optionally in the presence of a cocatalyst comprising anthracene or substituted anthracenes or their Mg adducts and/or magnesium halides.

3. The process according to claim 2, wherein the inorganic Grignard reagent catalyst is prepared by a process comprising reacting FeCl$_2$ or MnCl$_2$ with magnesium metal.

4. The process according to claim 2, wherein the inorganic Grignard reagent catalyst is prepared by a process comprising reacting CrCl$_3$ or MoCl$_5$ with magnesium metal.

5. The process according to claim 2, wherein aromatic chlorine compounds or chlorine containing polymers are employed as said organic halides.

6. The process according to claim 2, wherein tetrahydrofuran, monoglyme or diglyme is used as said solvent.

7. The process according to claim 2, wherein the reaction is performed at temperatures from 0° C. to the boiling point of the solvent employed.

8. The process according to claim 2, wherein finely divided magnesium powder, is used.

9. The process according to claim 2, 9,10-diphenylanthracene is used as a cocatalyst.

10. The process according to claim 2, wherein the reaction of organic chlorine compounds with magnesium powder is performed in the presence of catalysts prepared by reacting FeCl$_2$ or MnCl$_2$, 9,10-diphenylanthracene, MgCl$_2$ and excess Mg powder in THF, monoglyme or diglyme.

11. The process according to claim 8, wherein the finely divided magnesium powder is >200 mesh.

* * * * *